United States Patent [19]

Nishimura et al.

[11] Patent Number: 4,657,535
[45] Date of Patent: Apr. 14, 1987

[54] MEDICAL NEEDLE DEVICE AND MEDICAL EQUIPMENT HAVING THE SAME

[75] Inventors: Tetsuro Nishimura; Nobukazu Tanokura; Masahiro Urushibata, all of Fujinomiya, Japan

[73] Assignee: Terumo Kabushiki Kaisha, Tokyo, Japan

[21] Appl. No.: 734,094

[22] Filed: May 15, 1985

[30] Foreign Application Priority Data

May 16, 1984 [JP] Japan ................................. 59-97695

[51] Int. Cl.[4] .......................................... A61M 5/32
[52] U.S. Cl. ................................... 604/263; 604/199; 604/411
[58] Field of Search ............... 604/414, 263, 192–199, 604/408–410

[56] References Cited

U.S. PATENT DOCUMENTS

| 3,523,530 | 8/1970 | Pagones | 604/263 |
| 4,091,811 | 5/1978 | Bates et al. | 604/263 |
| 4,435,177 | 3/1984 | Kuhlemann | 604/263 |
| 4,508,534 | 4/1985 | Garver et al. | 604/263 X |

Primary Examiner—Stephen C. Pellegrino
Attorney, Agent, or Firm—Cushman, Darby & Cushman

[57] ABSTRACT

A heat sterilized medical needle device having a needle cannula with a pointed distal end, a hub supporting a proximal end portion of the needle cannula at one end thereof and allowing connection of a tube at the other end thereof to allow communication between the tube and the needle cannula therethrough, and a protector comprising a hollow body with a closed distal end and an open proximal end and sealing a portion of the needle cannula which is exposed from the hub within the hollow portion thereof. The hub has a thin portion to be twisted and broken to disconnect the hub from the protector, and the hub is coupled to the protector to form a liquid-tight joint by blocking at a portion of the hub which is closer to the pointed end of the needle cannula than the thin portion.

8 Claims, 5 Drawing Figures

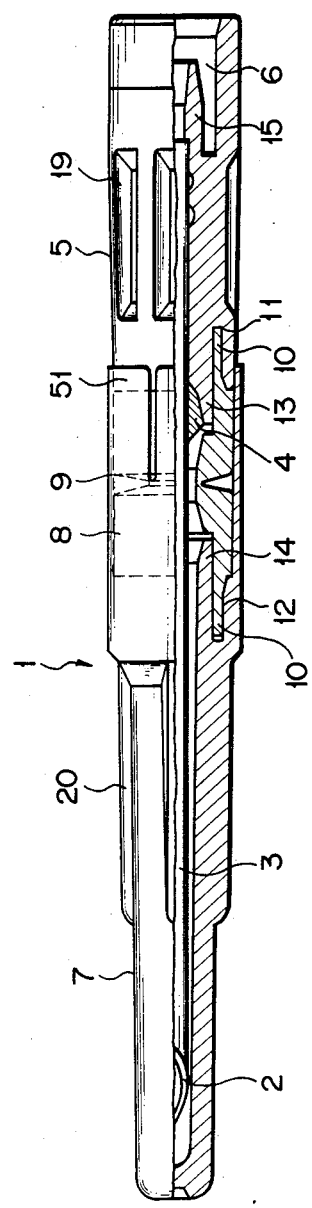
F I G. 5

MEDICAL NEEDLE DEVICE AND MEDICAL EQUIPMENT HAVING THE SAME

BACKGROUND OF THE INVENTION

1. Field of the Invention

The present invention relates to a medical needle device and medical equipment having the same.

2. Description of the Prior Art

Medical needle devices having an integrally formed hub and protector to improve its tamperproof property and ensure good hygiene are known (U.S. Pat. No. 3,523,530). In such a medical needle device, when a hub and a protector are formed integrally with each other, a thin fragile portion is formed therebetween. Before the medical needle device is used, the thin fragile portion is twisted and broken to expose the cannula. Although integral formation of the hub and protector seems convenient, many problems are presented as will be described below. That is, a highly advanced technique is required to form an integral thin assembly of a hub and a protector. In addition, it is difficult to form a thin fragile portion simultaneously with the hub and protector. As a result, a portion to be formed thin is formed thick. When such a thick portion is formed between the hub and protector, the force required for twisting and breaking this portion must be increased, and variations among devices are increased. A mold for forming the assembly must have high precision and is therefore expensive. Moreover, since a hub and a protector must be formed integrally, they are formed of the same material. Although the hub through which a needle cannula extends is strong, the protector connected thereto is hollow and has a relatively small wall thickness. The protector therefore is easily deformed. In order to prevent this, the protector must be made relatively thick. In general, a medical needle device is connected to a tube of a vinyl chloride resin. For this reason, the material for integrally forming the hub and protector is limited.

Another medical needle device is known wherein an outer surface of a portion around a fitting portion between a hub and a protector is coated with a plastic film (Japanese Utility Model No. 55-49075). However, this film is subject to peeling or damage, resulting in poor liquid-tightness.

SUMMARY OF THE INVENTION

It is, therefore, an object of the present invention to provide a medical needle device which is easy to manufacture, has a thin, fragile disconnecting portion of a uniform quality which allows easy disconnection of the device at the fragile portion by a given force to expose the needle cannula, and also to provide medical equipment having such a medical needle device.

According to a first aspect of the present invention, there is provided a heat sterilized medical needle device having a needle cannula with a pointed distal end, a hub supporting a proximal end portion of the needle cannula at one end thereof and allowing connection of a tube at the other end thereof to allow communication between the tube and the needle cannula therethrough, and a protector consisting of a hollow body with a closed distal end and an open proximal end and sealing a portion of the needle cannula which is exposed from the hub within the hollow portion thereof. The hub has a thin portion to be twisted and broken to disconnect the hub from the protector, and the hub is coupled to the protector to form a liquid-tight joint by blocking at a portion of the hub which is closer to the pointed end of the needle cannula than the thin portion.

According to a second aspect of the present invention, there is provided medical equipment comprising a container for containing a liquid therein, a medical needle device, and a tube, the heat sterilized medical needle device comprising a needle cannula with a pointed distal end, a hub supporting a proximal end portion of the needle cannula at one end thereof and allowing connection of the tube at the other end thereof to allow communication between the tube and the needle cannula therethrough, and a protector comprising a hollow body with a closed distal end and an open proximal end and sealing a portion of the needle cannula which is exposed from the hub within the hollow portion thereof, the hub having a thin portion to be twisted and broken to disconnect the hub from the protector, the hub being coupled to the protector to form a liquid-tight joint by blocking at a portion of the hub which is closer to the pointed end of the needle cannula than the thin portion, and the tube having one end connected to the proximal end of the hub to communicate with the needle cannula and the other end connected and communicating with the container.

The hub preferably includes a tube connecting portion, and a coupling portion for coupling the tube connecting portion and the protector. The thin portion is formed in the coupling portion, and the tube connecting portion and the coupling portion are coupled by blocking.

The protector and the tube connecting portion preferably comprises of polycarbonate, and the coupling portion preferably comprises a vinyl chloride resin.

BRIEF DESCRIPTION OF THE DRAWINGS

FIG. 5 is a longitudinal partial cross section of a medical needle device according to the present invention.

DETAILED DESCRIPTION OF THE PREFERRED EMBODIMENTS

The preferred embodiment of the present invention will be described in detail below with reference to the accompanying drawings.

Figure 1:
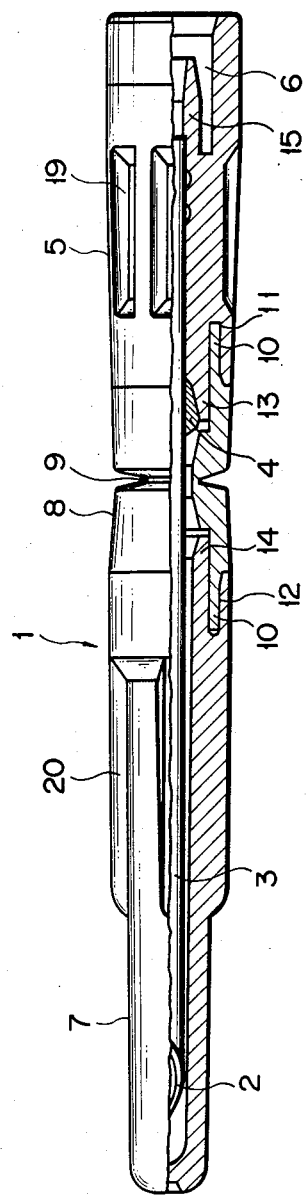
FIG. 1 is a longitudinal partial cross section of a medical needle device according to the present invention.

FIG. 1 is a longitudinal partial cross section of a medical needle device 1 according to the present invention. A needle cannula 3 has a pointed distal end 2 and a proximal end connected to a hub 5 with an adhesive 4 (e.g., an epoxy resin). An annular recess 6 is formed at the proximal end of the hub 5 and allows connection of a connecting tube (not shown). When the connecting tube is connected to the hub, the recess 6 allows communication between the tube and the needle cannula 3. A portion of the needle cannula which is exposed outside the hub 5 is covered with a protector 7. Conventionally, this portion of the needle cannula is protected by forming an integral assembly of a hub and a protector or forming a film between a hub and a protector. However, these methods are prone to the problems described above. However, according to the present invention, a coupler 8 is formed between the hub and protector, and the hub and protector are coupled by blocking performed by a heat treatment such as autoclaving, thereby liquid-tightly sealing the hub and protector. "Blocking" as used herein means adhesion between two members by heat without substantially melting the interface between the two members. The blocking temperature is lower than the melting point of a material of the two members.

As shown in FIG. 1, the coupler 8 is a tubular member having an annular thin portion 9 at its center. Although the coupler 8 need not be symmetrical about the thin portion 9, the coupler 8 is preferably so formed in view of easy manufacture and assembly of the coupler 8 with the hub 5 and protector 7. Tubular legs 10 extending at the two sides of the thin portion 9 are respectively fitted in a recess 11 formed at the distal end of the hub 5 and a recess 12 formed at the proximal end portion of the protector 7. The sizes of the recesses 11 and 12 and the legs 10 of the coupler 8 are such that the legs 10 can be easily inserted in the recesses 11 and 12 and, during heat treatment, the material constituting the coupler 8 and the legs 10 shrinks to adhere projections 13 and 14 of the hub 5 and the protector 7 by blocking, thereby guaranteeing liquid-tightness. If sufficient liquid-tightness and tamperproofness cannot be obtained by blocking the coupler 8 with the hub 5 and the protector 7, an adhesive can be applied between these members. A nonsolvent adhesive is preferably used, and a UV curing adhesive is particularly preferable.

The coupler 8 is coupled with the hub 5 and the protector 7 mainly by blocking. Therefore, a combination of materials constituting these members can be suitably selected if the materials allow blocking. It is preferable to use materials having different thermal shrinkage coefficients to facilitate blocking. The hub 5 and the protector 7 need not shrink upon application of heat and can therefore consist of a material such as polycarbonate, a vinyl chloride resin, or an MBS resin. From the viewpoints of preventing deformation and improving heat resistance during autoclaving, the hub 5 and the protector 7 preferably consist of polycarbonate. In contrast to this, the coupler 8 is fitted in the recesses 11 and 12 of the hub 5 and the protector 7, respectively, so as to adhere them by blocking upon thermal shrinkage, thereby guaranteeing liquid-tightness and that they are tamperproof. The coupler 8 is preferably made of a material softer than the hub and the protector, such as a hard vinyl chloride resin, polycarbonate or MBS resin and more preferably consists of hard or soft polyvinyl chloride in view of how easy it is broken by twisting.

The connecting tube (not shown) consists of a vinyl chloride resin. The tube is connected to the hub 5 consisting of, e.g., polycarbonate, by fitting the tube in a recess 6 of the hub 5 and adhering it to an inner projection 15 of the hub 5 by the heat of autoclaving.

Since the coupler 8 is formed as a separate material and is of a different material from that of the hub 5 and the protector 7, the thin portion 9 having a thickness allowing easy twisting and breaking can be formed in the coupler 8 with high precision. The shape of the coupler 8 or its coupling state with the hub 5 and the protector 7 can be freely selected as long as it has the thin portion 9 for twisting and breaking and allows blocking with the hub 5 and the protector 7.

As described above, blocking means adhesion between two members by heat such as the heat of autoclaving and without requiring a means such as a solvent or adhesive.

The coupler can be formed integrally with the hub. Therefore, the hub can consist of the tube connecting portion and the coupling portion. Materials of respective members of the device according to the present invention must be selected in consideration of the following.

Polyvinyl chloride and polycarbonate have a higher blocking adhesion strength than that between polyvinyl chloride pieces.

Polyvinyl chloride shrinks easily but polycarbonate hardly shrinks upon application of heat. When polyvinyl chloride is located outside polycarbonate, the polyvinyl chloride tightly holds the polycarbonate and causes firm blocking.

In order to allow observation of the cannula surface, the protector must be transparent. In view of this requirement, polycarbonate is preferably used for the protector rather than polyvinyl chloride.

Since the protector generally is thin, polycarbonate which is less liable to shrink upon application of heat is preferred. Polyvinyl chloride may cause thermal deformation and damage the cannula.

Although the tube connecting portion can consist of polyvinyl chloride, polycarbonate is preferably used since it is less liable to thermal deformation and tends not to decrease adhesion strength with the cannula.

When the connecting portion deforms after the adhesive between the tube connecting portion and cannula hardens, a gap may be formed between the adhesive layer and the cannula.

Figure 2:
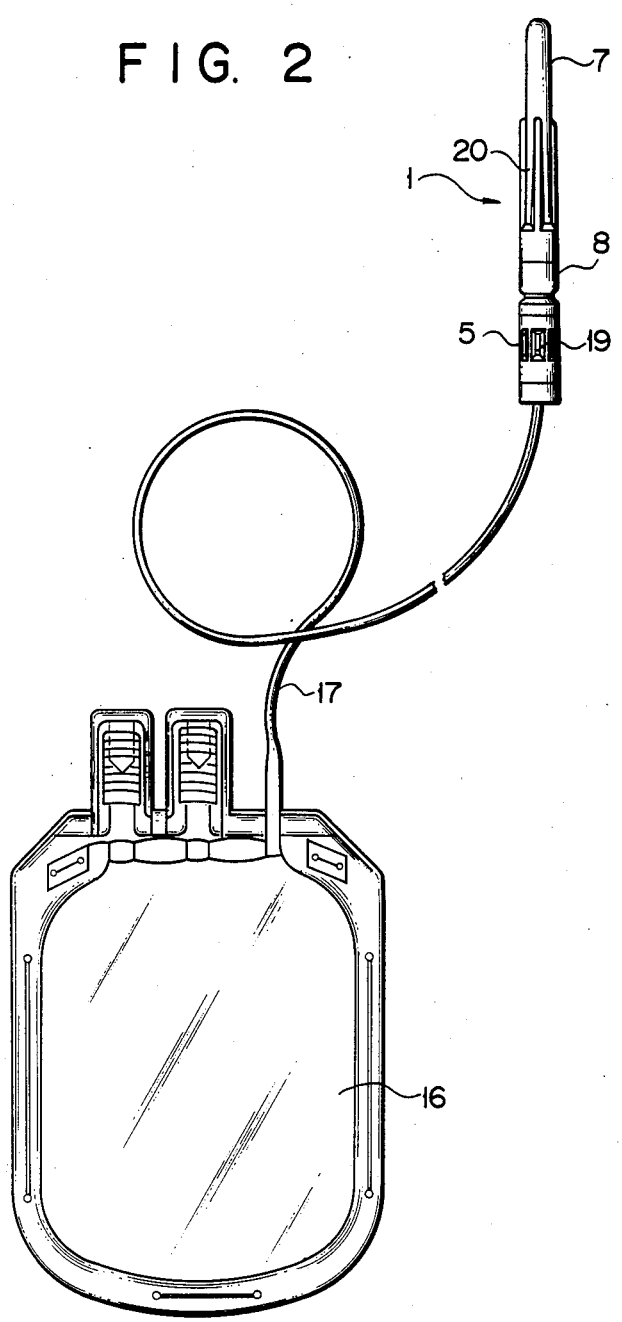
FIG. 2 is a plan view of medical equipment having the medical needle device according to the present invention.

The medical needle device 1 described above is connected to one of various blood collecting containers. FIG. 2 shows an enlarged view of the device connected to a blood bag as one example of blood collecting containers. Referring to FIG. 2, reference numeral 16 denotes a blood bag; and 17, a connecting tube. The connecting tube 17 and a sheet of the blood bag 16 are preferably adhered by RF welding.

Vinyl chloride resins used herein include homopolymers of vinyl chloride and copolymers thereof with vinylidene chloride, vinyl acetate or vinyl alcohol. In the case of a copolymer, a monomer content must be 15 mol % or less and is preferably 3 to 7 mol %.

A medical needle device and medical equipment having the same according to the present invention are manufactured and used in the manner to be described below.

Figure 3:
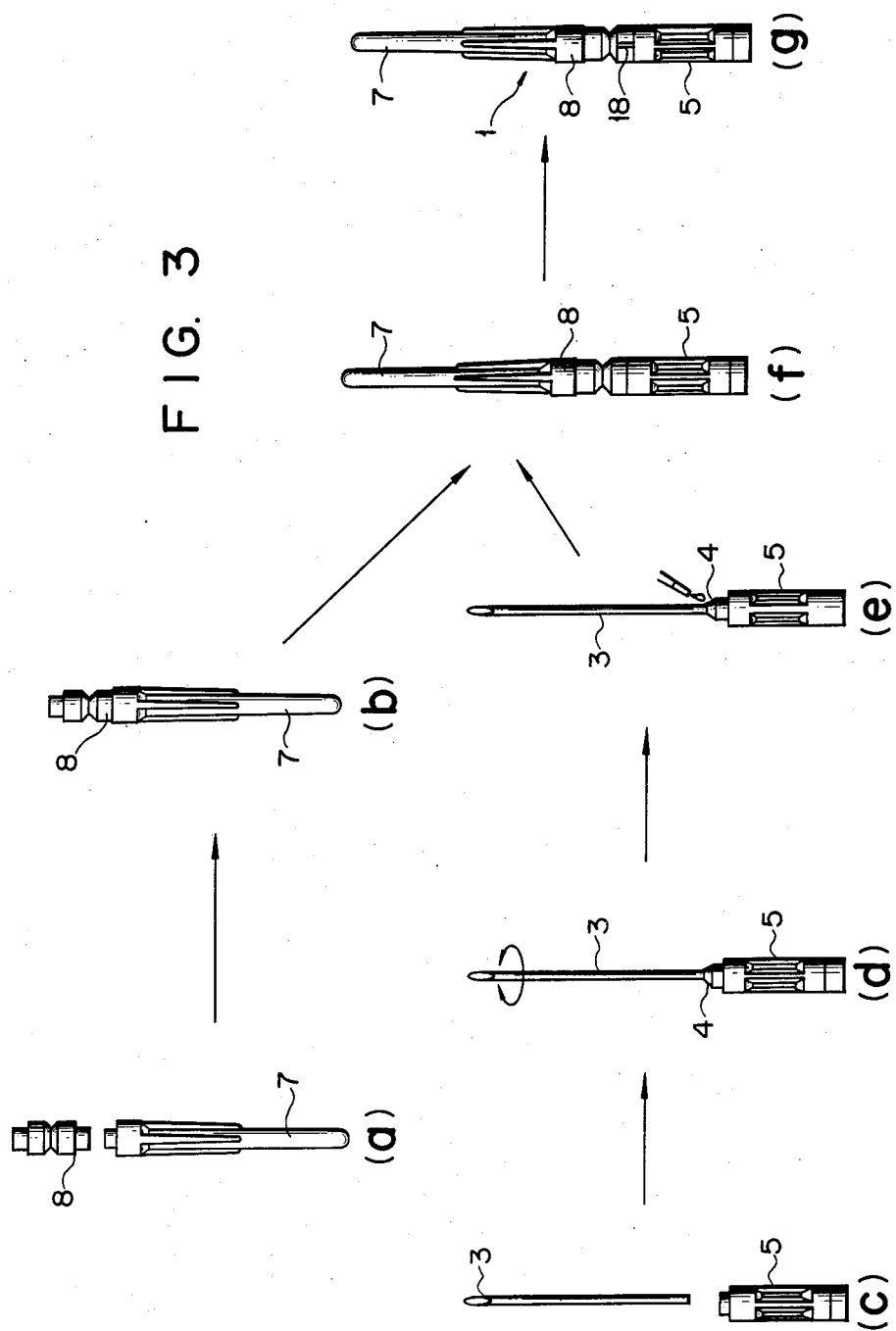
FIG. 3 is an assembly flow chart of the medical needle device according to the present invention.

As shown in the assembly flow chart of the medical needle device in FIG. 3, after the protector 7 and the coupler 8 are aligned as shown in FIG. 3(a), they are fitted with each other as shown in FIG. 3(b). Similarly, after the needle cannula 3 and the hub 5 are aligned as shown in FIG. 3(c), they are adhered with the adhesive 4 as shown in FIG. 3(d). After applying a filler (UV curing adhesive) between the coupler 8 and the hub 5 or the protector 7, if required, as shown in FIG. 3(e), the hub 5 and the protector 7 are coupled using the coupler 8 as a coupling medium, as shown in FIG. 3(f). A mark 18 is formed on the coupler 8 so as to allow confirmation of that it is tamperproof, as shown in FIG. 3(g). The medical needle device assembled in this manner itself or medical equipment having it is autoclaved as shown in FIG. 2. When the medical equipment is autoclaved, since the material of the coupler 8 undergoes more thermal shrinkage than that of the hub 5 and the protector 7, the coupler 8 firmly holds and blocks the hub 5 and the protector 7 so as to guarantee liquid-tightness over a long period of time. When a UV curing adhesive is used, UV irradiation is performed in a suitable step.

Figure 4:
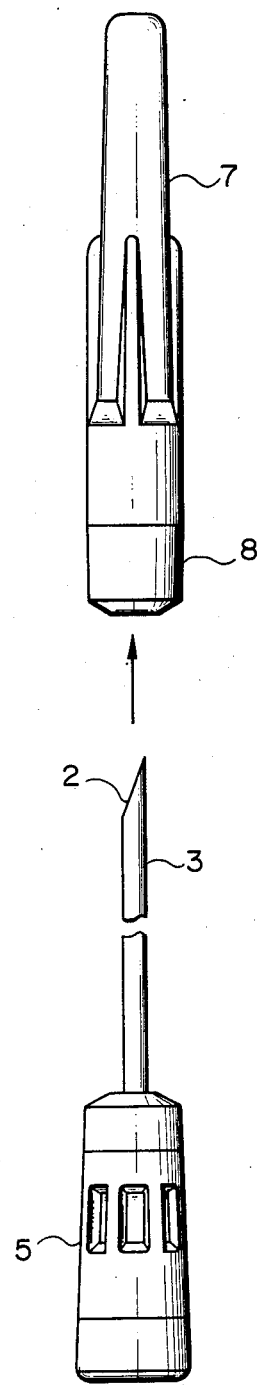
FIG. 4 is a side view showing the medical needle device according to the present invention in a state wherein the hub and protector are separated by twisting the fragile portion.

The medical needle device and medical equipment using it are used as connected to a blood collecting container as shown in FIG. 2. Before the device or medical equipment having it is used, ribs 19 and 20 formed on the hub 5 and the protector 7 are held by fingers to apply torsional force in opposite directions. Then, the thin portion 9 preferably having an annular shape and formed on the coupler 8 is twisted and broken so as to release part of the coupler 8 and the protector 7 from the hub 5 and the remaining part of the coupler 8. Thus, the needle cannula 3 is exposed. This state is shown in FIG. 4. The distal end 2 of the needle cannula 3 is pierced into a suitable portion of a patient's body to collect blood. The collected blood is supplied to a blood collecting container 16 from the needle cannula 3 through a tube 17.

The twisting force for breaking the thin portion 9 can be a predetermined small force since the thin portion 9 is very thin and there is not quality variation from one device to another. Since the hub 5 and the protector 7 consist of a heat-resistant material and the coupler 8 consists of a material having a relatively large thermal shrinkage coefficient, the hub 5 and the protector 7 will not deform to damage the needle cannula 3 during autoclaving. Furthermore, since the coupler 8 undergoes more thermal shrinkage than the hub 5 and the protector 7, it firmly holds and blocks the hub 5 and the protector 7. In this manner, blocking adhesion is performed to provide a satisfactory liquid-tightness over a long period of time.

When the protector 7 is remounted on the needle cannula 3 after the medical needle device is used, i.e., after the thin portion formed in the coupler is twisted off, the pointed needle cannula may remain exposed until safely disposed if the protector 7 drops. In order to prevent this, in accordance with another embodiment of the present invention, at least one holder is formed at the proximal end of the protector such that the holder extends from the proximal end portion of the protector 7 along its axial direction and has one end engaging with the outer surface of the hub. The protector 7 separated from the hub is stably held onto the hub 5 since the protector 7 is engaged with the outer surface of the hub at the end of the holder.

This embodiment is illustrated in FIG. 5. A medical needle device shown in FIG. 5 is the same as shown in FIG. 1 except that in the former a proximal end portion of a protector 7 has at least one integrally formed holder 51 which extends to the outer surface of the hub 5. In general, a thin portion 9 of a coupler 8 is very thin and easily deforms upon autoclaving. For this reason, the protector may be inclined at a maximum angle of about 5 degrees upon sterilization by autoclaving. That is, the protector may be inclined at an angle corresponding to the clearance between the outer surface of the needle cannula and the inner surface of the protector. When such deformation occurs, the outer surface of the needle cannula 3 contacts the inner surface of the protector 7. Then, it may become difficult to remove the protector 7 after twisting off the thin portion 9 or to remount it on the hub 5. The holder 51 prevents this problem.

A plurality of such holders 51 are preferably arranged at equal intervals along the circumferential direction of the device. With this arrangement, deformation of the thin portion 9 of the coupler 8 upon autoclaving is prevented, and sliding movement between the protector 7 and the needle cannula 3 after autoclaving can be performed smoothly. Such a plurality of holders 51 can comprise a plurality of split sleeves formed integrally with the proximal end of the protector 7.

A medical needle device and medical equipment according to the present invention have many advantages to be described below as compared to conventional devices.

(1) A hub and a protector are not formed integrally with each other but are coupled through a separate coupler. The material of the hub and protector has a small thermal shrinkage coefficient, and the material of the coupler has a large thermal shrinkage coefficient. For these reasons, when autoclaving of the device is performed, the hub and protector will not thermally deform and damage the needle cannula, but the coupler fitted on the hub and protector thermally shrinks to cause firm and liquid-tight blocking. Excellent tamperproofness is guaranteed.

(2) The coupler is a member separate from the hub and the protector. Therefore, the thin portion to be twisted off before use of the device is sufficiently thin and only a small predetermined force is required to twist it off.

(3) When a non-solvent type adhesive such as a UV curing resin is used to couple the coupler with the hub and the protector, these members can be held in position more firmly. Furthermore, since solvent is not used, excess solvent will not be introduced into the device, and degradation or cracking of the material of the device will not be caused. The working environment for coupling the coupler with the hub and the protector is not degraded.

(4) As compared to the manufacture of a conventional device wherein a hub and a protector are formed integrally with each other, a high precision mold is not required, and a fragile thin portion can be easily formed. A sufficiently thin portion can be formed between the hub and protector. Devices will not be damaged during distribution on the market, and variations in twisting force prior to use of the devices are eliminated.

What is claimed is:

1. A heat sterilized medical needle device comprising:
a needle cannula with a pointed distal end,
a hub comprised of a low thermal shrinkable material and supporting a proximal end portion of said needle cannula at one end thereof and allowing connection of a tube at the other end thereof to allow communication between said tube and said cannula therethrough, and
a protector comprised of a low thermal shrinkable material and having a hollow body with a closed distal end and an open proximal end and sealing a portion of said needle cannula which is exposed from said hub within the hollow portion thereof,
said hub having a thin portion to be twisted and broken to disconnect said hub from said protector,
said hub being coupled to said protector to form a liquid-tight joint by heating in heat sterilization of the whole medical needle device carried out at a temperature below the melting point of the midical needle device at a portion of said hub which is closer to the pointed end of said needle cannula than said thin portion, wherein said hub includes a tube connecting portion and a coupling portion coupling said tube connecting and said protector, said thin portion is formed at said coupling portion, and said tube connecting portion and said coupling portion are coupled by blocking, said coupling portion being comprised of a large thermal shrinkable material.

2. A device according to claim 1, wherein said protector and said tube connecting portion consist of polycarbonate, and said coupling portion consists of a vinyl chloride resin.

3. A device according to claim 1, wherein said protector has at least one holder means which extends from the proximal end thereof along an axial direction thereof and which has an end portion engaging with an outer surface of said hub.

4. A device according to claim 3, wherein said holder means comprises a split sleeve formed integrally with the proximal end of said protector.

5. Medical equipment comprising a container for containing a liquid therein, a heat sterilized medical needle device, and a tube, said medical needle device comprising a needle cannula with a pointed distal end, a hub supporting a proximal end portion of said needle cannula at one end thereof and allowing connection of the tube at the other end thereof to allow communication between said tube and said needle cannula therethrough, and a protector comprising a hollow body with a closed distal end and an open proximal end and sealing a portion of said needle cannula which is exposed from said hub within the hollow portion thereof, said hub having a thin portion to be twisted and broken to disconnect said hub from said protector, said hub being coupled to said protector to form a liquid-tight joint by heating in heat sterilization of the whole medical needle device carried out at a temperature below the melting point of the medical needle device at a portion of said hub which is closer to the pointed end of said needle cannula than said thin portion, and said tube having one end connected to the proximal end of said hub to communicate with said needle cannula and the other end connected and communicating with said container, said hub consisting of a tube connecting portion and a coupling portion coupling said tube connecting portion and said protector, said thin portion being formed at said coupling portion, and said tube connecting portion and said coupling portion being coupled by blocking.

6. Equipment according to claim 5, wherein said protector and said tube connecting portion consist of polycarbonate, and said coupling portion consists of a vinyl chloride resin.

7. Equipment according to claim 5, wherein said protector has at least one holder means which extends from the proximal end thereof along an axial direction thereof and which has an end portion engaging with an outer surface of said hub.

8. Equipment according to claim 7, wherein said holder means comprises a split sleeve formed integrally with the proximal end of said protector.

* * * * *

UNITED STATES PATENT AND TRADEMARK OFFICE
CERTIFICATE OF CORRECTION

PATENT NO. : 4,657,535
DATED : Apr. 14, 1987
INVENTOR(S) : NISHIMURA et al

It is certified that error appears in the above-identified patent and that said Letters Patent is hereby corrected as shown below:

In the claims,

Claim 1, column 6, line 56, after "said tube and said" insert --needle--.

Claim 1, column 6, line 68, change "midical" to --medical--.

Signed and Sealed this

Sixteenth Day of February, 1988

Attest:

DONALD J. QUIGG

*Attesting Officer*    *Commissioner of Patents and Trademarks*